United States Patent [19]

Godfroid et al.

[11] Patent Number: 5,500,426
[45] Date of Patent: Mar. 19, 1996

[54] SUBSTITUTED PIPERAZINES FOR TREATMENT OF NON-INSULIN-DEPENDANT DIABETES

[75] Inventors: Jean-Jacques Godfroid, Paris; Aazdine Lamouri, Bagneux; Estera Touboul, Paris; Xuan Wang, L'Hay les Roses; Pierre Renard, Versailles; Bruno Pfeiffer, Eaubonne; Béatrice Guardiola, Saint Cloud, all of France

[73] Assignee: Adir et Compagnie, Courbevoie, France

[21] Appl. No.: 425,953

[22] Filed: Apr. 19, 1995

Related U.S. Application Data

[62] Division of Ser. No. 278,396, Jul. 21, 1994.

[30] Foreign Application Priority Data

Jul. 23, 1993 [FR] France ................ 93 09088

[51] Int. Cl.$^6$ .................... A61K 31/495; A61K 31/535; C07D 403/04; C07D 413/04
[52] U.S. Cl. .................... 514/252; 514/228.8; 544/295; 544/369; 544/370
[58] Field of Search .................... 514/252, 256, 514/228.8

[56] References Cited

U.S. PATENT DOCUMENTS

| 2,562,036 | 7/1951 | Hultquist et al. | 260/250 |
| 3,557,135 | 1/1971 | Marchetti | 260/307 |
| 4,959,368 | 9/1990 | Awaya et al. | 514/252 |
| 5,091,428 | 2/1992 | Paschal et al. | 514/252 |

OTHER PUBLICATIONS

Nathani, P., Indian Journal of Chemistry, "2,3–Disubstituted Quinazolinones and Their Antiparkinsonian Activity", vol. 28B (1989) pp. 745–750 Month of Publication not Provided.

Street, L., J. Med. Chem., "Synthesis and Biological Activity of 1,2,4–Oxadiazo Derivatives: Highly Potent and Efficacious Agonists for Cortical Muscarinic Receptors", 33, (1990), 2690–2697 Month of Publication not Provided.

Kuzmierkiewicz, W., Scientia Pharmaceutica, "3,5–Disubstituted Derivatives of 1,2,4–Triazole Synthesis and Hypotensive Activity", 53, (1985) 133–138 Month of Publication not Provided.

*Primary Examiner*—Nicholas Rizzo
*Assistant Examiner*—King L. Wong
*Attorney, Agent, or Firm*—Gordon W. Hueschen

[57] ABSTRACT

A compound selected from those of formula (I):

$$\begin{array}{c} R_1 \\ | \\ N \end{array} \begin{array}{c} (CH_2)_n - A \\ R_3 \\ N \\ | \\ R_2 \end{array} \quad (I)$$

in which

A represents $$\begin{array}{c} N \\ \diagdown \diagup R_5 \\ X - (CH_2)_m \end{array}$$

X represents N—R$_4$ or oxygen, and R$_1$, R$_2$, R$_3$, R$_4$, R$_5$, n and m are as defined in the description, useful in improving glucose tolerance in the treatment of non-insulin-dependent diabetes.

7 Claims, No Drawings

SUBSTITUTED PIPERAZINES FOR TREATMENT OF NON-INSULIN-DEPENDANT DIABETES

The present application is a division of our prior-filed application Ser. No. 08/278,396, filed Jul. 21, 1994, now allowed.

The present invention relates to new substituted piperazines, to a process for the preparation thereof, and to pharmaceutical compositions containing them.

The literature provides several examples of substituted piperazines. There may be mentioned especially the works of L. J. Street et al. (*J. Med. Chem.*, 33(10), (1990), 2690–2697) in which there are disclosed piperazines that are substituted in the 2-position by oxadiazole groups and that can be used as agonists of the central muscarinic receptors.

Other publications describe piperazine derivatives that can be used in the treatment of Parkinson's disease (*Indian J. Chem.*, 28B.(9), (1989), 745–750) or that have hypotensive activity (*Sci. Pharm.*, 53(3), (1985), 133–138).

The Applicant has found a new group of substituted piperazines that have pharmacological properties which are unexpected for this type of molecule, and that are very valuable for the treatment of non-insulin-dependent diabetes.

More precisely, the invention relates to new piperazines of the general formula (I):

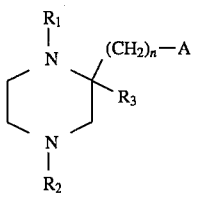

in which:
  $R_1$ and $R_2$, each independently of the other, are selected from hydrogen and alkyl, cycloalkyl, monocycloalkylalkyl, dicyclo-alkylalkyl, aryl and arylalkyl, each of those radicals being optionally substituted,
  $R_3$ is selected from hydrogen and alkyl,
  n has a value selected from 0, 1 and 2, and
  A represents

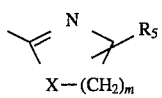

in which
    X is selected from oxygen and N—$R_4$,
    m has a value selected from 1 and 2,
    $R_4$ is selected from hydrogen and optionally substituted alkyl, alkoxycarbonyl and aryloxycarbonyl, and
    $R_5$ is selected from hydrogen and alkyl,
  wherein:
    the terms "alkyl", "alkoxy", "monocyclo-alkylalkyl", "dicyclo-alylalkyl", "arylalkyl" and "alkoxycarbonyl" denote radicals the hydrocarbon chain of which has 1 to 10 carbon atoms inclusive in a straight or branched chain,
    the term "cycloalkyl" denotes cyclic hydrocarbon radicals having 3 to 8 carbon atoms inclusive,
    the terms "aryl", "arylalkyl" and "aryloxycarbonyl" relate to radicals the aromatic part of which is selected from phenyl and naphthyl and, the expression "optionally substituted" means that the radicals so described may be substituted by one or more chemical entities selected from alkyl, hydroxy, alkoxy, halogen, haloalkyl, polyhaloalkyl, nitro, amino, alkylamino and polyalkylamino, their stereoisomers, N-oxides and pharmaceutically-acceptable acid or base addition salts.

The present invention relates also to a process for the preparation of the compounds of formula (I), characterised in that:

a) the compound of formula (II):

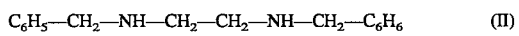

is brought to reflux in an aromatic solvent, for example benzene or toluene, in the presence of triethylamine with the dibromide of formula (III):

in which Alk represents a linear or branched alkyl radical having from 1 to 4 carbon atoms, to give the compound of formula (IV):

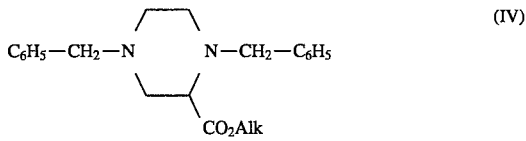

in which Alk is as defined above, which is then debenzylated by the action of hydrogen in the presence of a catalyst, such as palladium-on-carbon in absolute ethanol, to give the compound of formula (V):

in which Alk is as defined above, which is then converted into the compound of formula (Va), (Vb) or (Vc):

in which Arak represents an optionally substituted arylalkyl radical as defined above, and Alk is as defined above, for the compound of formula (Va):
  after protection of the nitrogen atom in the 4-position by triphenylmethyl chloride in a suitable solvent, such as methylene chloride, in the presence of triethylamine, by treatment with Arak-Cl in the presence of potassium carbonate and of a catalytic amount of potassium iodide, in a suitable solvent, such as cold acetone, and then deprotection of the nitrogen atom in the 4-position by means of gaseous hydrogen chloride in a suitable solvent, such as ethanol or a concentrated hydrochloric acid/acetone mixture, for the compounds of formulae (Vb) and (Vc):

by treatment of the compound of formula (V) directly with Arak-Cl in toluene at reflux in the presence of triethylamine, and then separation of the mono- and di-substituted compounds by chromatography over a silica gel column, b) or, the compound of formula (VI):

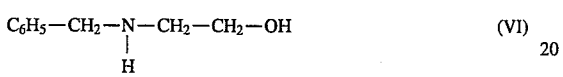

is optionally treated with a ketone or an aldehyde, in an acidic and alcoholic medium, for example formic or acetic acid and methanol, the ketone or aldehyde chosen being the homologue of the radical $R'_1$ ($R'_1$ having the same definition as $R_1$, with the exception of hydrogen) that is to be bonded to the nitrogen atom, for example formaldehyde when $R'_1$ represents the methyl radical, and cyclohexanone when $R'_1$ represents the cyclohexyl radical, in order to obtain the compound of formula (VII):

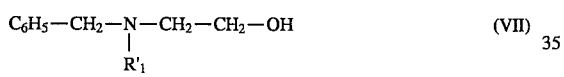

in which $R'_1$ is as defined above, which compounds of formulae (VI) and (VII), when treated with a chlorinating agent, such as thionyl chloride, yield the corresponding chlorinated compounds and then, under the action of a saturated aqueous ammonia solution, yield the compound of formula (VIII):

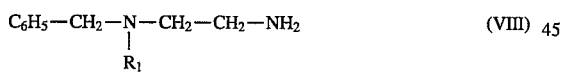

in which $R_1$ is as defined above, which compound is then optionally treated, like the compound of formula (VI), with the homologue of the radical $R'_2$ ($R'_2$ having the same definition as $R_2$, with the exception of hydrogen) in the form of an aldehyde or ketone, and, after hydrogenation of the double bond that is formed, for example by means of sodium borohydride, yields the diamine of formula (IX):

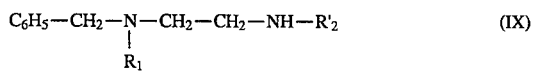

in which $R_1$ and $R'_2$ are as defined above, the compounds of formulae (VIII) and (IX) then being debenzylated according to the process described for the compound of formula (IV) and then treated with the dibromide of formula (III) described above to give, after separation of any isomers by chromatography and/or crystallisation, the compound of formula (X):

in which $R_1$, $R_2$ and Alk are as defined above, c) or, the compound of formula (VI):

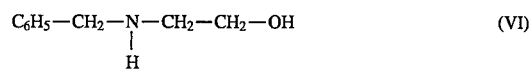

is optionally treated with a ketone or an aldehyde, in an acidic and alcoholic medium, for example acetic acid and methanol, the ketone or aldehyde chosen being the homologue of the radical $R'_2$ ($R'_2$ having the same definition as $R_2$, with the exception of hydrogen) that is to be bonded to the nitrogen atom, for example formaldehyde when $R'_2$ represents the methyl radical, and cyclohexanone when $R'_2$ represents the cyclohexyl radical, in order to obtain the compound of formula (XI):

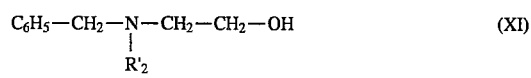

in which $R'_2$ is as defined above, which compounds of formulae (VI) and (XI), when treated with a chlorinating agent, such as thionyl chloride, yield the corresponding chlorinated compounds which, when treated with benzylamine, yield the diamine of formula (XII):

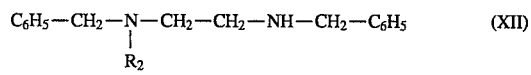

in which $R_2$ is as defined above, which, by reaction with a halogenated compound of formula (XIII):

in which X represents a halogen atom and Alk is as defined above, yields the diamine of formula (XIV):

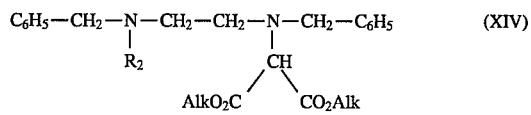

in which Alk and $R_2$ are as defined above, which, after metallisation and reaction with a halogenated compound of formula (XV):

in which X and $R_3$ are as defined above, yields the diamine of formula (XVI):

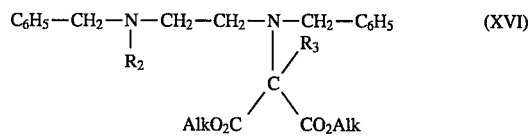

in which $R_2$, $R_3$ and Alk are as defined above, which, after catalytic debenzylation and cyclisation, yields the piperazinone of formula (XVII):

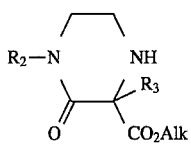
(XVII)

in which $R_2$, $R_3$ and Alk are as defined above, which:

either by the action of aldehyde or ketone precursors of the radical $R'_1$ according to the method described above, or by direct alkylation with a halogenated compound of formula (XVIII):

$$R'_1\text{—}X \quad (XVIII),$$

in which $R'_1$ and X are as defined above, yields the piperazinone of the general formula (XIX):

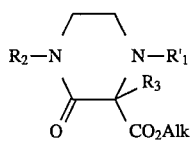
(XIX)

in which $R'_1$, $R_2$, $R_3$ and Alk are as defined above, which piperazinones of formulae (XIX) and (XVII), by reduction with boron hydrides, yield the piperazine of formula (XX):

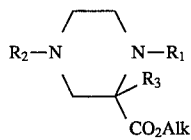
(XX)

in which $R_1$, $R_2$, $R_3$ and Alk are as defined above, it likewise being possible for the secondary amines of the compounds of formulae (V), (Va) and (Vb) to be substituted:

either by the action of aldehyde or ketone precursors of the radicals $R'_1$ or $R'_2$ according to the method described above, or by direct alkylation with a halogenated compound of formula (XXI):

$$R\text{—}X \quad (XXI)$$

in which R has the same definition as $R'_1$ or $R'_2$ and X represents a halogen, with, in the case of the compounds of formula (V), optional protection beforehand of the most reactive nitrogen atom by a triphenylmethyl group, as indicated for the preparation of the compound of formula (Va), the compounds of formulae (V), (Va), (Vb) and (Vc), their optional products of substitutions as discussed above, and the compounds of formula (X) likewise forming pan of the compounds of formula (XX), which compounds of formula (XX) may optionally be converted into their higher homologues of formula (XXII):

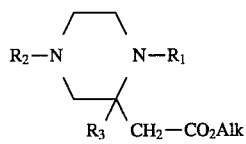
(XXII)

in which $R_1$, $R_2$, $R_3$ and Alk are as defined above, by treatment with a reducing agent, for example lithium aluminium hydride, in order to convert the ester function into an alcohol function, and then chlorination, for example by the action of thionyl chloride, followed by treatment with an alkaline earth metal cyanide, for example potassium cyanide, and finally conversion of the resulting nitrile into an ester by the action of an alcohol in an acidic medium, for example an ethanol/concentrated sulfuric acid mixture, which compound of formula (XXII), when optionally subjected to the same treatment, yields the homologue of formula (XXIII):

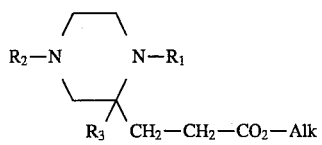
(XXIII)

in which $R_1$, $R_2$, $R_3$ and Alk are as defined above, all the compounds of formulae (XX), (XXII) and (XXIII) forming the compounds of formula (XXIV) in their entirety:

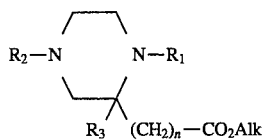
(XXIV)

in which $R_1$, $R_2$, $R_3$, Alk and n are as defined above, which compounds of formula (XXIV) are subjected:

either: a) to the action of a diamine of formula (XXV):

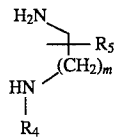
(XXV)

in which $R_4$, $R_5$ and m are as defined above, in the presence of a trialkylaluminium, for example trimethylaluminium, in an anhydrous aprotic solvent, such as toluene, at reflux, to give the compound of formula (Ia):

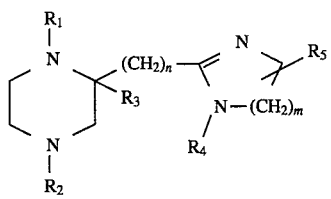
(Ia)

in which $R_1$, $R_2$, $R_3$, $R_4$, $R_5$, n and m are as defined above, or: b) to the action of the compound of formula (XXVI):

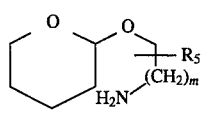
(XXVI)

in which $R_5$ and m are as defined above, which compound is obtained from the corresponding α,ω-hydroxy-amine, the amine function of which has previously been protected by conversion to N,N-dibenzyl-α,ω-hydroxy-amine, by the action of benzyl chloride, and then protection of the alcohol function by dihydropyran, and then hydrogenolysis in the presence of palladium-on-carbon in order to free the amine function, the compound of formula (XXVI) reacting with the compound of formula (XXIV) under the same conditions as the compound of formula (XXV) to give the compound of formula (XXVII):

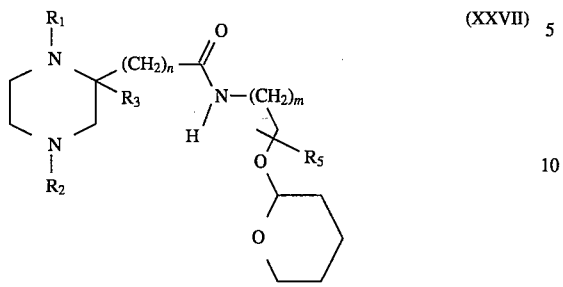

in which $R_1$, $R_2$, $R_3$, $R_5$, n and m are as defined above, the alcohol function of which compound is freed in an acidic alcoholic medium, for example a hydrochloric acid/methanol mixture, and then converted into the corresponding chloride by the action of thionyl chloride in order to permit the desired cyclisation, in a basic medium, for example sodium hydroxide, and obtain the compound of formula (Ib):

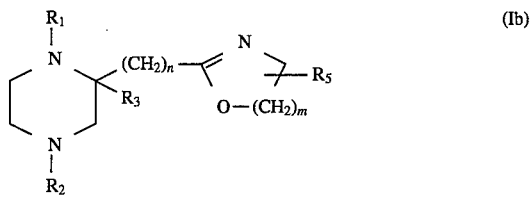

in which $R_1$, $R_2$, $R_3$, $R_5$, n and m are as defined above, all the compounds of formulae (Ia) and (Ib) forming the compounds of formula (I) in their entirety, which compounds are purified and, optionally, separated into their stereoisomers by a conventional separation method and which are, if desired, converted into their N-oxides or into their pharmaceutically-acceptable acid or base addition salts.

The compounds of the present invention possess a very powerful anti-diabetic activity. They bring about a very marked improvement in glucose tolerance in vivo in animal models of type II diabetes (non-insulin-dependent), whether they be administered orally, intraperitoneally or intravenously.

The compounds of the invention do not appear to have great affinity for the a (alpha) and 62 (beta) adrenergic receptors.

After being tested orally in rats, the compounds of the invention proved to be non-toxic at doses of up to 1 g/kg. Their powerful activity, coupled with their low toxicity, renders the compounds of the invention especially valuable for the treatment of non-insulin-dependent diabetes.

The present invention relates also to pharmaceutical compositions containing at least one compound of formula (I) or an N-oxide thereof or an addition salt thereof with a pharmaceutically acceptable acid or base, on its own or in combination with one or more inert, non-toxic excipients. Of the pharmaceutical compositions according to the invention there may be mentioned in particular those which are suitable for oral, parenteral, nasal, rectal, perlingual, ocular or pulmonary administration, and especially injectable preparations, aerosols, ocular or nasal drops, tablets, film-coated tablets, dragées, gelatin capsules, suppositories, capsules, creams, ointments, dermic gels, etc.

The dosage used varies according to the age and weight of the patient, the mode of administration and the nature of the disorder and of any associated treatment, and ranges from 0.5 mg to 1 g per 24 hour period.

The following Examples illustrate the invention without limiting it in any way.

Starting materials are available or are prepared by means of known processes.

Preparation A 1,4-dibenzyl-2-ethoxycarbonylpiperazine (dihydrochloride)

80 g (0.31 mol) of ethyl 2,3-dibromopropionate diluted in 300 ml of benzene are added dropwise, but fairly rapidly, to a warm solution of 72 g (0.3 mol) of N,N'-dibenzylethylenediamine, 700 ml of benzene and 50 ml (0.36 mol) of triethylamine. After the addition, reflux is maintained for 3 hours (triethylamine hydrobromide precipitates in the reaction mixture). The mixture is cooled and filtered through fritted glass, and the solid is washed with ether. The filtrate is washed with 200 ml of saturated sodium hydrogen carbonate solution and then twice with 100 ml of water. The organic phases are dried over magnesium sulfate and the solvents are evaporated off in vacuo. Approximately 100 ml of toluene are added, and evaporation is continued. The resulting residue is diluted in 400 ml of absolute ethanol and saturated with gaseous hydrogen chloride. The salt precipitates by the addition of ether. Filtering, washing with ether and drying yield from 100 to 110 g of white crystals.

Yield: 89%

Preparation B 2-ethoxycarbonylpiperazine (dihydrochloride)

600 mg of 10% palladium-on-carbon are added to 41.1 g (0.1 mol) of the compound obtained in Preparation A suspended in 300 ml of absolute ethanol. The mixture is stirred and heated at 40° C. for 12 hours under a hydrogen atmosphere. The catalyst is removed by filtration and the title compound precipitates by the addition of ether. From 20 to 21 g of white crystals are obtained.

Yield: 86–91%

Preparation C 2,4-dimethyl-2-ethoxy carbonyl-1-(2,4-dichlorobenzyl)piperazine

Step a: N-benzyl-N-methylaminoethanol

A mixture consisting of 151 g (1 mol) of N-benzylaminoethanol, 120 ml of 90% formic acid, 120 ml of a 35% aqueous formaldehyde solution and 1 liter of methanol is heated under reflux for 20 hours. The solvent is evaporated off in vacuo and the residue is treated with an aqueous sodium hydroxide solution and then extracted with methylene chloride. After customary treatment, the product is purified by distillation. 138 g of the desired product are obtained.

Boiling point: (2021 Pa) 140°–142° C. Yield: 84%

Step b: N-benzyl-N-(2-chloroethyl)methylamine 70 ml (0.96 mol) of thionyl chloride in 70 ml of trichloromethane are added dropwise to 130 g (0.79 mol) of the compound obtained in Step a dissolved in 400 ml of trichloromethane. The mixture is stirred for 15 hours at room temperature and the solvent is evaporated off in vacuo. The residue is recrystallised from an acetone/methanol mixture. 155 g of white crystals corresponding to the desired product are obtained.

Melting point: 140.5° C.

Step c: N,N'-dibenzyl-N-methyl-1,2-diaminoethane 128 g (0.7 mol) of the compound obtained in Step b dissolved in 600 ml of ethanol are added dropwise to 150 g (1.4 mol) of benzylamine diluted in 200 ml of warm ethanol. The mixture is stirred at room temperature for 24 hours and the solvent is evaporated off in vacuo. Benzylamine hydrochloride crystallises from a mixture of methylene chloride and acetone, and is removed by filtration. The filtrates are saturated with gaseous hydrogen chloride and the hydrochloride of the desired compound crystallises from a methylene chloride/ether mixture. 105 g of white crystals are obtained.

Yield: 46%

Step d: Diethyl 2-{N-[2-(N'-methylbenzylamino)ethyl]benzylamino}malonate 100 g (0.5 mol) of the compound obtained in Step c dissolved in 600 ml of methylene chloride are added to 62 g (0.3 mol) of ethyl bromomalonate. The reaction mixture is stirred at room temperature for 24 hours and the organic phase is washed with water. Customary treatment of the organic phase yields 80 g of the desired compound in the form of a colourless oil.

Yield: 65%

Step e: Diethyl 2-{N-[2-(N'-methylbenzylamino)ethyl]-benzylamino}-2-methylmalonate 7.8 g of 60% sodium hydride in oil and 70 ml of dimethylformamide are added dropwise, while cold, to 80 g (0.195 mol) of the diester obtained above diluted in 140 ml of dimethylformamide. When the evolution of gas has ceased, 12.14 ml (0.195 mol) of methyl iodide in 35 ml of dimethylformamide are added dropwise. The reaction is stirred at room temperature overnight. The resulting precipitate is filtered off after the addition of ether. Customary treatment of the organic phase yields 75 g of the desired compound.

Yield: 90%

Step f: Ethyl 1,3-dimethyl-2-oxopiperazine-3-carboxylate 75 g of the compound obtained in Step e in 500 ml of absolute ethanol and 100 mg of 10% palladium-on-carbon are stirred and heated at 45° C. under a hydrogen atmosphere for 48 hours. After filtration, the solvent is evaporated off and the residue is purified by chromatography over a silica gel column (eluant: methylene chloride, and then 5% methanol). 20 g of colourless oil are obtained.

Yield: 60%

Step g: Ethyl 1-(2,4-dichlorobenzyl)-2,4-dimethyl-3-oxopiperazine-2-carboxylate 43 g of potassium carbonate and 4.3 g of potassium iodide are added to 20 g (0.107 mol) of the compound obtained in the preceding step dissolved in 650 ml of acetone. A solution of 0.128 mol of 2,4-dichlorobenzyl chloride in 100 ml of acetone is added dropwise. The mixture is then stirred at room temperature for several hours. The salts are removed by filtration. Customary treatment of the organic phase yields the desired compound, which crystallises from an ether/hexane mixture.

Step h: Ethyl 1-(2,4-dichlorobenzyl)-2,4-dimethylpiperazine-2-carboxylate 4.4 ml of fleshly distilled boron trifluoride are added dropwise, while cold, to 1.1 g of dry sodium borohydride suspended in 35 ml of freshly distilled tetrahydrofuran. The reaction mixture is stirred at 0° C. for 2 hours and then 3.5 g (0.01 mol) of the compound obtained in Step g in 100 ml of tetrahydrofuran are added. The mixture is then heated under reflux for one hour and then 50 ml of a 2N hydrochloric acid solution are added while cold. The mixture is neutralised with sodium hydroxide and then extracted with ether. Customary treatment of the organic phase yields a crude product which is purified over a silica gel column (eluant: trichloromethane). 1 g of the pure desired product is obtained in the form of a colourless oil.

Yield: 30%

EXAMPLE 1

1-(2-chlorobenzyl)-4-methyl-2-(4,5-dihydro[1H]imidazol-2-yl)piperazine

Step a: 4-triphenylmethyl-2-ethoxycarbonylpiperazine 28 g (0.1 mol) of triphenylmethyl chloride diluted in 300 ml of methylene chloride are added dropwise to a mixture, cooled to −10° C., of 23.1 g (0.1 mol) of the compound obtained in Preparation B, 400 ml of methylene chloride and 55 ml (0.4 mol) of triethylamine. After the addition, the mixture is stirred overnight. 21 g of sodium carbonate dissolved in 200 ml of water are then added. The organic phase is separated off, washed with a saturated sodium chloride solution and dried over magnesium sulfate, and the solvent is evaporated off in vacuo. Approximately 50 ml of toluene are added, and evaporation is continued. The residue crystallises from hexane/ether (9:1) and yields 26 g of white crystals. The filtrate is purified by chromatography over a silica gel column, eluant: firstly petroleum ether/ether (7:3), and then pure ether. 6 g of pure crystallised product are obtained.

Yield: 80%

Step b: 1-(2-chlorobenzyl)-2-ethoxycarbonylpiperazine

A mixture of 40 g (0.1 mol) of the compound obtained in Step a, 400 ml of acetone, 40 g of potassium carbonate, 4 g of potassium iodide and 19 g (0.12 mol) of 2-chlorobenzyl chloride is stirred for 15 hours at room temperature. After customary treatment of the organic phase, the solvents are evaporated off in vacuo and the resulting residue is dissolved in 300 ml of acetone; 300 ml of acetone containing 25 ml of concentrated hydrochloric acid are added. The mixture is stirred for 2 hours at room temperature. Treatment of the organic phase yields 19 g of the desired product.

Yield: 80%

Step c: 1-(2-chlorobenzyl)-4-methyl-2-ethoxycarbonylpiperazine

A mixture of 28 g (0.1 mol) of the compound obtained in Step b, 120 ml of methanol, 12 ml of 37% formaldehyde and 12 ml of formic acid is heated under reflux for 20 hours. The solvent is evaporated off in vacuo and the resulting residue is taken up in ether and a saturated sodium hydrogen carbonate solution. The organic phase is washed, neutralised and then extracted with ether. After drying over magnesium sulfate and evaporation of the solvent, the residue is dissolved in 200 ml of absolute ethanol and saturated with gaseous hydrochloric acid. The dihydrochloride precipitates by the addition of ether. 32 g of white crystals are isolated.

Yield: 86.5%

Step d: 1-(2-chlorobenzyl)-4-methyl-2-(4,5-dihydro[1H]imidazol-2-yl)piperazine 75 ml of a 2M solution of trimethylaluminium in toluene are added to 200 ml of anhydrous toluene. The mixture is cooled in ice, and 4 ml (0.06 mol) of ethylenediamine are added. The mixture is brought to room temperature and then 9.5 g (0.032 mol) of the compound obtained in the preceding step are added, in 80 ml of toluene. The mixture is heated under reflux for 5 hours. All the operations are carried out under an argon atmosphere. After being left overnight at room temperature, the reaction mixture is hydrolysed with 100 ml of methanol/water solution (8:2). After filtration, the solvents are evaporated off in vacuo, the residue is dissolved in methylene chloride, and the organic phase is washed with a saturated sodium chloride solution and then with a 2N hydrochloric acid solution. Extraction with methylene chloride yields 7 g of the title product, which is purified by recrystallisation from a hexane/ether mixture to yield 4 g of pure product.

Yield: 70% Melting point: 98.5°–99° C.

The compounds of Examples 2 to 13 are obtained by the same procedure using the appropriate aryl chloride in Step b.

EXAMPLE 2

1-(4-chlorobenzyl)-2-(4,5-dihydro[1H]imidazol-2-yl)-4-methylpiperazine

Yield: 49% Melting point: 198°–200° C. (trihydrochloride dihydrate)

EXAMPLE 3

1-(2-methoxybenzyl)-2-(4,5-dihydro[1H]imidazol-2-yl)-4-methylpiperazine

Yield: 36% Melting point: 168°–170° C. (trihydrochloride dihydrate)

EXAMPLE 4

1-(3-methoxybenzyl)-2-(4,5-dihydro[1H]imidazol-2-yl)-4-methylpiperazine

Yield: 38% Melting point: 78°–80° C. (dihydrochloride 1.5 hydrate)

EXAMPLE 5

1-(2,3-dimethoxybenzyl)-2-(4,5-dihydro[1H] imidazol-2-yl)-4-methylpiperazine

Yield: 41% Melting point: 160°–162° C. (dihydrochloride monohydrate)

EXAMPLE 6

1-(2,3-dichlorobenzyl)-4-methyl-2-(4,5-dihydro [1H]imidazol-2-yl)piperazine

Yield: 58% Melting point: 158°–160° C. (decomposition) (dihydrochloride monohydrate)

EXAMPLE 7

1-(2,4-dichlorobenzyl)-2-(4,5-dihydro[1H]imidazol-2-yl)-4-methylpiperazine

Yield: 60% Melting point: 167°–169° C. (dihydrochloride monohydrate)

EXAMPLE 8

1-benzyl-2-(4,5-dihydro[1H]imidazol-2-yl)-4-methyipiperazine

Yield: 55% Melting point: 166°–168° C. (dihydrochloride 0.75 hydrate)

EXAMPLE 9

1-(2-fluorobenzyl)-2-(4,5-dihydro[1H]imidazol-2-yl)-4-methylpiperazine

Yield: 37% Melting point: 160°–162° C. (dihydrochloride dihydrate)

EXAMPLE 10

1-(2,6-dichiorobenzyl)-2-(4,5-dihydro[1H]imidazol-2-yl)-4-methylpiperazine

Yield: 43% Melting point: 182°–184° C. (dihydrochloride monohydrate)

EXAMPLE 11

1-(3,4,5-trimethoxybenzyl)-2-(4,5-dihydro[1H] imidazol-2-yl)-4-methylpiperazine

Yield: 45% Melting point: 185°–187° C. (dihydrochloride monohydrate)

EXAMPLE 12

1-(2-methylbenzyl)-2-(4,5-dihydro[1H]imidazol-2-yl)-4-methyipiperazine

Yield: 51% Melting point: 156°–158° C. (dihydrochloride 1.5 hydrate)

EXAMPLE 13

1-(2-trifluoromethylphenyl)-2-(4,5-dihydro[1H] imidazol-2-yl)-4-methylpiperazine Yield: 45% Melting point: 163°–165° C. (dihydrochloride monohydrate)

EXAMPLE 14

1-methyl-2-(4,5-dihydro[1H]imidazol-2-yl)-4-(2-chlorobenzyl)piperazine

A solution of 23 g of the compound obtained in Preparation B and 55 ml of triethylamine in 300 ml of toluene is heated to reflux. 16.1 g (0.1 mol) of 2-chlorobenzyl chloride dissolved in 200 ml of toluene are added dropwise. After the addition, the mixture is heated for 3 hours. The mixture is cooled and the organic phase is treated in the customary manner. The residue is purified by chromatography over a silica gel column (eluant: petroleum ether/ether 3:7, and then ether) in order to isolate 10 g of monobenzylated compound, which is then treated according to the process described in Example 1, Step c et seq. Purification by flash chromatography also allows 11 g of 1,4-[di-(2-chlorobenzyl)]-2-ethoxycarbonylpiperazine to be isolated, which is used for preparing the compound of Example 16.

Yield: 62% (from 1-methyl-4-(2-chlorobenzyl)-2-ethoxycarbonylpiperazine) Melting point: 140°–142° C. (decomposition) (trihydrochloride monohydrate)

EXAMPLE 15

1-methyl-2-(4,5-dihydro[1H]imidazol-2-yl)-4-(2, 4-dichlorobenzyl)piperazine

The title product is obtained by following the procedure of Example 14 but replacing 2-chlorobenzyl chloride with 2,4-dichlorobenzyl chloride.

EXAMPLE 16

1,4-[di-(2-chlorobenzyl)]-2-(4,5-dihydro[1H]imidazol-2-yl)piperazine

This compound is obtained according to the process described in Example 14 by collecting the disubstituted compound at the time of the purification over a silica gel column.

Yield: 67% (from 1,4-[di-(2-chlorobenzyl)]-2-ethoxycarbonylpiperazine) Melting point: 86°–90° C. (trihydrochloride dihydrate)

The compounds of Examples 17 and 18 below are obtained by following the same procedure as in Example 16 and replacing 2-chlorobenzyl chloride in Example 14 with the appropriate benzyl chlorides:

EXAMPLE 17

1,4-[di-(2,4-dichlorobenzyl)]-2-(4,5-dihydro[1H]imidazol-2-yl)piperazine

Yield: 62% Melting point: 188°–190° C. (dihydrochloride monohydrate)

EXAMPLE 18

1,4-dibenzyl-2-(4,5-dihydro[1H]imidazol-2-yl)piperazine

EXAMPLE 19

1,4-dibenzyl-2-[(4,5-dihydro[1H]imidazol-2-yl)methyl]piperazine

Step a: 1,4-dibenzyl-2-hydroxymethylpiperazine 5 g (131 mmol) of lithium aluminium hydride are stirred in 200 ml of dry tetrahydrofuran and kept at 0° C. in an ice-bath. A solution of 60 g (175 mmol) of the compound obtained in Preparation A dissolved in 200 ml of anhydrous tetrahydrofuran is then added dropwise. The mixture is stirred at 0° C. for one hour and then at room temperature for 24 hours. The excess lithium aluminium hydride is then decomposed at 0° C. by the addition of a 20% sodium hydroxide solution. After filtration of the resulting aluminium hydroxide, the organic phase is evaporated off and the resulting residue is crystallised from hexane, yielding 48.3 g of white crystals of the desired product.

Yield: 92%

Step b: 1,4-dibenzyl-2-chloromethylpiperazine 5.92 ml (81 mmol) of thionyl chloride are added dropwise to 20 g (67.6 mmol) of the compound obtained in the preceding step dissolved in 200 ml of benzene. The mixture is stirred for 3 hours at room temperature. After evaporation of the benzene, the resulting residue is taken up in chloroform and washed 3 times with water until the pH is neutral. The organic phase is dried over magnesium sulfate, filtered and evaporated off, and the resulting residue is chromatographed over a silica gel column (eluant: ether/petroleum ether 10:90), yielding 17 g of the desired product in the form of an oil.

Yield: 80%

Step c: 1,4-dibenzyl-2-cyanomethylpiperazine

A mixture of 4.57 g (70.2 mmol) of potassium cyanide and 10 ml of water is heated to reflux. When the potassium cyanide has dissolved, 17 g (54 mmol) of the chloride obtained in Step b dissolved in 10 ml of ethanol are added slowly. When the addition is complete, the mixture is heated under reflux for 3 hours. After evaporation of the solvent, the mixture is taken up in chloroform and washed with water until the pH is neutral. The chloroform phase is dried over magnesium sulfate, filtered and evaporated off. The resulting residue is crystallised from hexane and yields 13.2 g of white crystals.

Yield: 80%

Step d: 1,4-dibenzyl-2-ethoxycarbonylmethylpiperazine 10 g of concentrated sulfuric acid and 30 g of absolute ethanol are added to 13.2 g (43.3 mmol) of the compound obtained in Step c. The mixture is heated under reflux (120° C.) for 3 hours. The excess ethanol is distilled off and the resulting residue is taken up in an aqueous sodium carbonate solution and extracted with chloroform. The organic phase is dried over magnesium sulfate, filtered and evaporated off. The resulting residue is chromatographed over a silica gel column (eluant: ether/petroleum ether 10:90), yielding 11.4 g of the desired product in the form of an oil.

Yield: 75%

Step e: 1,4-dibenzyl-2-[(4,5-dihydro[1H]imidazol-2-yl)methyl]piperazine

Identical procedure to that used for Example 1, Step d, starting from the ester obtained in the preceding step.

Yield: 47% Melting point: 176°–178° C. (trihydrochloride dihydrate)

EXAMPLE 20

1-(2-methoxybenzyl)-2-[(4,5-dihydro[1H]imidazol-2-yl)methyl]-4-methylpiperazine

Compound obtained in a manner identical to that described for Example 3, starting from the ester obtained in Example 19, Step d.

EXAMPLE 21

1-(2-chlorobenzyl)-2-(4,5-dihydro[1H]imidazol-2-yl)-4-n-propylpiperazine

The compound obtained in Example 1, Step b, is treated in acetone with n-propyl chloride in the presence of potassium iodide and potassium carbonate. The resulting 1-(2-chlorobenzyl)-4-n-propyl-2-ethoxycarbonylpiperazine is then treated as described in Example 1, Step d.

Yield: 65% Melting point: 160°–163° C. (decomposition) (trihydrochloride monohydrate)

EXAMPLE 22

1-(2-chlorobenzyl)-2-(4,5-dihydro[1H]imidazol-2-yl)-4-isopropylpiperazine

Identical process to that described in the preceding Example, replacing n-propyl chloride with isopropyl bromide.

Yield: 54% Melting point: 156° C. (decomposition) (dihydrochloride monohydrate)

EXAMPLE 23

1-(2-chlorobenzyl)-2-(4,5-dihydro[1H]imidazol-2-yl)-4-ethylpiperazine

Compound obtained according to an identical process, replacing n-propyl chloride with ethyl bromide.

Yield: 30% Melting point: 163° C. (decomposition) (dihydrochloride)

The compounds of the following two Examples are obtained according to the same process as that described in Example 14, replacing each instance of methylation by means of formaldehyde with alkylation with the appropriate alkyl halide according to the method described in Example 21.

EXAMPLE 24

1-ethyl-2-(4,5-dihydro[1H]imidazol-2-yl)-4-(2-chlorobenzyl)piperazine

Yield: 64% Melting point: 139° C.

EXAMPLE 25

1-isopropyl-2-(4,5-dihydro[1H]imidazol-2-yl)-4-(2-chlorobenzyl)piperazine

Yield: 58% Melting point: 159° C. (trihydrochloride)

EXAMPLE 26

1-(2-chlorobenzyl)-2-(4,5-dihydro[1H]imidazol-2-yl)piperazine

Identical procedure to that described in Example 1, omitting Step c.

Yield: 28% Melting point: 161 ° C. (decomposition) (trihydrochloride monohydrate)

EXAMPLE 27

1-(dicyclopropylmethyl)-2-(4,5-dihydro[1H]imidazol-2-yl)-4-methylpiperazine

Step a: N-methyl-N-benzyl-2-aminoethylamine 110 g (0.5 mol) of the chloride obtained in preparation C, step b, are suspended in 1 liter of water saturated with ammonia. The mixture is stirred for 3 days at room temperature; the solvent is partially evaporated off in vacuo and the solution is rendered basic by the addition of sodium hydroxide. The amine is extracted with methylene chloride and, after drying over magnesium sulfate and evaporation of the solvent, the product is purified by distillation. 49 g of the desired compound are obtained.

Yield: 60% Boiling point: (2000 Pa) 152°–154° C.

Step b: N-methyl-N-benzyl-2-(N'-dicyclopropylmethylamino)ethylamine

A mixture consisting of 8.2 g (0.05 mol) of the compound obtained in Step a, 5.5 g (0.05 mol) of dicyclopropyl ketone and 50 ml of cyclohexane is heated for 15 days. The solvent is evaporated off in vacuo and there are added to the residue 50 ml of dry, cold methanol and then 1.9 g (0.05 mol) of sodium borohydride. After stirring for 15 hours at room temperature, the solution is poured into 50 ml of water containing 2 g (0.05 mol) of sodium hydroxide, and is saturated with sodium chloride and then extracted with hexane. The product is purified over a silica column (eluant: pure methylene chloride and then methylene chloride/methanol 97:3). 6 g of the desired compound are obtained.

Yield: 47%

Step c: N-methyl-2-(N'-dicyclopropylmethylamino)ethylamine 5.8 g of the compound obtained in Step b, in 30 ml of absolute ethanol, and 100 mg of 10% palladium-on-carbon are stirred and heated at 45° C. under a hydrogen atmosphere for 3 hours. The solvent is evaporated off. After customary treatment of the organic phase, the desired crude product is purified by distillation.

Yield: 85% Boiling point: (6.66 Pa) 48°–52° C.

Step d: 1-dicyclopropylmethyl-2-ethoxycarbonyl-4-methylpiperazine

A mixture consisting of 4.4 g (0.026 mol) of the diamine obtained above, 10 ml of triethylamine and 50 ml of benzene is heated to reflux, and then 6.4 g (0.0246 mol) of methyl 2,3-dibromopropionate in 20 ml of benzene are added. After heating under reflux for 3 hours, the mixture is cooled and filtered. The solution is washed with water and, after customary treatment, the residue is purified by chromatography over a silica column (eluant: ether). 5.1 g of the desired pure compound are obtained.

Yield: 78%

Step e: 1-(dicyclopropylmethyl)-2-(4,5-dihydro[1H]imidazol-2-yl)-4-methylpiperazine The ester obtained in Step d above is subjected to the reaction described in Example 1, Step d.

Yield: 50% Melting point: 98° C.

EXAMPLE 28

1,4-diisopropyl-2-(4,5-dihydro[1H]imidazol-2-yl)piperazine

Reacting 2-ethoxyxarbonylpiperazine with 2,2 equivalents of isopropyl bromide in the same conditions as for example 21, and treating the obtained product in the same conditions as for example 1, step d, the desired product is obtained.

Yield: 35% Melting point: 145° C. (decomposition) (trihydrochloride dihydrate)

EXAMPLE 29

1-(2-chlorobenzyl)-2-(4,5-dihydro[1H]oxazol-2-yl)-4-methylpiperazine

Step a: 2-[(tetrahydropyran-2-yl)oxy]ethylamine

One mole of 2-aminoethanol is put together with two equivalents of benzyl chloride and triethylamine in solution in ethanol. The hydroxy-amine hydrochloride so protected is subjected to the action of dihydropyran in solution in methylene chloride, and then the amine is deprotected by the action of gaseous hydrogen in the presence of catalyst (palladium-on-carbon).

Step b: 1-(2-chlorobenzyl)-2-[(2-hydroxyethylamino)carbonyl]-4-methylpiperazine 7.3 g (0.05 mol) of the compound obtained in Step a are diluted in 80 ml of anhydrous toluene. The solution is degassed and cooled by means of an ice-bath, and then 25 ml (0.05 mol) of a 2M trimethylaluminium solution in toluene are added. After the addition, the mixture is brought to room temperature and 10 g (0.034 mol) of the compound obtained in Example 1, Step c, are added. The reaction mixture is heated under reflux for 4 hours and then hydrolysed with 100 ml of a methanol/water solution (8:2). The precipitate that forms is filtered off, the solvents are evaporated off in vacuo., and the residue is dissolved in methylene chloride. The organic phase is washed with water and dried over magnesium sulfate, and the solvent is again evaporated off in vacuo. The crude product is taken up in methanol and a saturated solution of gaseous hydrochloric acid. The mixture is stirred for 2 hours at room temperature, the solvent is evaporated off in vacuo, and the salt is dissolved in water. The aqueous phase is extracted with methylene chloride and then neutralised with sodium carbonate. Customary treatment yields 7.3 g of the desired compound in the form of an oil.

Yield: 69%

Step c: 1-(2-chlorobenzyl)-2-[(2-chloroethylamino)carbonyl]-4-methylpiperazine 2.7 ml (0.037 mol) of thionyl chloride diluted in 10 ml of chloroform are added dropwise to 7 g (0.027 mol) of the compound obtained in the preceding step in 50 ml of chloroform cooled in an ice-bath. The mixture is stirred for 15 hours at room temperature and then poured into 60 ml of a 1M sodium carbonate solution. After customary treatment, the product is purified over a silica column (eluant: ether/petroleum ether 1:1, and then ether). The desired compound so purified is recrystallised from a hexane/ether mixture. 4.5 g of pale yellow crystals are isolated.

Yield: 50% Melting point: 74°–75° C.

Step d: 1-(2-chlorobenzyl)-2-(4,5-dihydro[1H]oxazol-2-yl)-4-methylpiperazine

A warm solution of 0.260 g (0.068 mol) of sodium hydroxide in 6 ml of 80% ethanol is added dropwise to a warm solution of 2.2 g (0.067 mol) of the chloride obtained above in 15 ml of ethanol. The mixture is heated under reflux for 30 minutes. The solvent is evaporated off in vacuo and the residue is taken up in ether. After customary treatment, 1.7 g of white crystals are isolated by crystallisation from hexane.

Yield: 85% Overall yield: 29% Melting point: 96.8° C.

EXAMPLE 30

1-methyl-4-(2-chlorobenzyl)-2-(4,5-dihydro[1H]oxazol-2-yl)piperazine

Identical procedure to that described for Example 14 up to the formation of the ester, and then formation of the oxazolinyl radical as described in Example 29.

EXAMPLE 31

1-dicyclopropyl-4-methyl-2-(4,5-dihydro[1H]oxazol-2-yl)piperazine

Identical procedure to that described for Example 30, starting with the procedure of Example 27.

EXAMPLE 32

1,4-dibenzyl-2-[(4,5-dihydro[1H]oxazol-2-yl)methyl]piperazine

Identical procedure to that described for Example 30, starting with the procedure of Example 19.

EXAMPLE 33

1,4-dibenzyl-2-[2-(4,5-dihydro[1H]imidazol-2-yl)ethyl]piperazine

The ester obtained in Step d of Example 19 is again subjected to Steps a, b, c, d and e of Example 19 to yield the title product.

EXAMPLE 34

1-methyl-4-(2-chlorobenzyl)-2-[2-(4,5-dihydro[1H]oxazol-2-yl)ethyl]piperazine

As obtained according to the procedure described in Example 33, starting from the ester obtained as intermediate in Example 30.

EXAMPLE 35

1,4-dibenzyl-2-[(1-phenoxycarbonyl)-4,5-dihydro[1H]imidazol-2-yl]piperazine

Compound obtained according to the procedure of Example 16 using, in order to form the imidazolinyl radical, N-phenyloxycarbonylethylenediamine instead of ethylenediamine.

Yield: 75% Melting point: 129°–131° C.

EXAMPLE 36

1,4-dibenzyl-2-[(2-methyl)-4,5-dihydro[1H]imidazol-2-yl]piperazine

Compound obtained according to the procedure of Example 16 using, in order to form the imidazolinyl radical, N-methylethylenediamine instead of ethylenediamine.

EXAMPLE 37

1-phenyl-4-(2-chlorobenzyl)-2-(4,5-dihydro[1H]imidazol-2-yl)piperazine

This compound is obtained according to Example 1, replacing 2-ethoxycarbonylpiperazine with 1-phenyl-2-ethoxycarbonylpiperazine obtained from N-phenyl-N'-benzylethylenediamine.

EXAMPLE 38

1-cyclohexyl-4-(2-chlorobenzyl)-2-(4,5-dihydro[1H]imidazol-2-yl)piperazine

This compound is obtained according to the method described in Example 24, replacing ethyl bromide with cyclohexyl bromide.

EXAMPLE 39

1-benzyl-4-methyl-2-(1,4,5,6-tetrahydro[1H]pyrimidin-2-yl)piperazine

Compound obtained according to the procedure described in Example 8, replacing ethylenediamine with 1,3-diaminopropane.

EXAMPLE 40

1-(2,4-dichlorobenzyl)-2-(4,5-dihydro[1H]imidazol-2-yl)-2,4-dimethylpiperazine

The desired compound is obtained following the procedure of Example 7 but replacing 4-methyl-2-ethoxycarbonyl-1-(2,4-dichlorobenzyl)piperazine in the final step with 2,4-dimethyl2-ethoxycarbonyl-1-(2,4-dichlorobenzyl)piperazine (Preparation C).

EXAMPLE 41

1,4-diisopropyl-2-(4,5-dihydro[1H]imidazol-2-yl)-2-methylpiperazine

Compound obtained according to a similar method to that described in Example 40.

EXAMPLE 42

1-(2,4-dichlorobenzyl)-4-methyl-2-(2-methyl-4,5-dihydro[1H]imidazol-2-yl)piperazine Compound obtained according to a similar procedure to that described for Example 36.

Melting point: 61°–63° C. (hydrochloride)

EXAMPLE 43

1-(2,4-dichlorobenzyl)-2-(5-methyl-4,5-dihydro[1H]imidazol-2-yl)-4-methylpiperazin Compound obtained according to an identical procedure to that of Example 7, but replacing ethylenediamine in the final step with 1,2-diaminopropane.

Melting point: 165°–167° C. (hydrochloride) (decomposition)

EXAMPLE 44

1-(2,4-dichlorobenzyl)-2-(3,4,5,6-tetrahydro[3H]pyrimidin-2-yl)-4-methylpiperazine Compound obtained according to an identical procedure to that of Example 7, but replacing ethylenediamine in the final step with 1,3-diaminopropane.

EXAMPLE 45

2-(4,5-dihydro[1H]imidazol-2-yl)-1,4-diisobutylpiperazine

Compound obtained according to a similar procedure to that described for example 28, but replacing isopropyl bromide with isobutyl bromide.

Melting point: 142°–144° C. (trihydrochloride monohydrate)

PHARMACOLOGICAL STUDY

EXAMPLE A

Demonstration of anti-diabetic activity

Effect of the products of the invention on glucose tolerance in rats rendered intolerant to glucose by a small dose of streptozotocine.

1) Experimental protocol 11-week-old male Wistar rats are treated with streptozotocine (35 mg/kg i.p.) in order partially to destroy the β-pancreatic cells. Only animals exhibiting glucose intolerance similar to that of type II diabetes were used in the experiments that followed (*THIBAULT et al., Endocrinology*, (1992), 130(5), 2521–2527).

The animals so selected are then pretreated (6 per dose) with the test compounds by the i.p., p.o. or i.v. route, 10 minutes before the administration of glucose (0.5 g/kg of body weight) by the i.v. route. The parameters representing glucidic metabolism are measured in comparison with control animals.

The procedure on each rat may be represented schematically as follows:

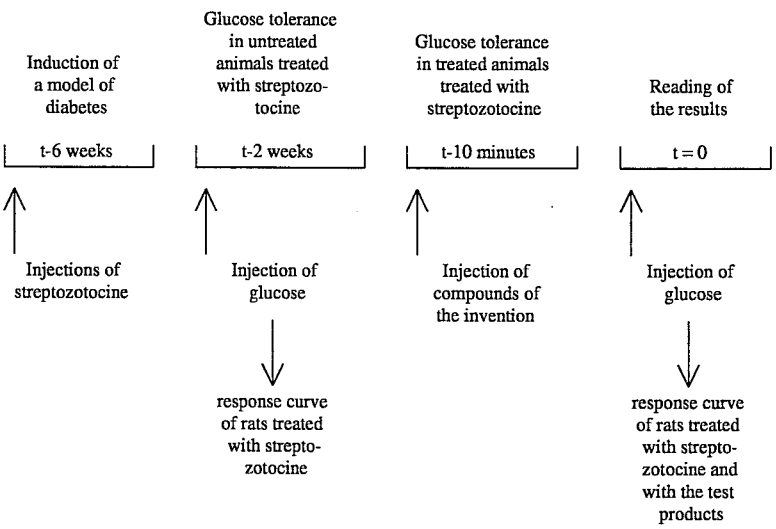

2) Results

Blood samples are taken 0, 5, 10, 15, 20, 25 and 30 minutes after the injection of glucose. The concentrations of glucose in the blood are then determined. Glucose tolerance is then assessed by:

the determination of ΔG, which represents the integration of the variations in glycaemia below the basal level during the test. A reduction in ΔG following administration of a test compound is an indication of anti-diabetic activity;

the determination of the K coefficient, which represents the slope of the fall in the glucose concentrations, taking account of the assimilation of glucose. The higher the value of the K coefficient, the better the activity of the test product.

The products of the invention prove to be remarkably active in this test. In fact, they are responsible for a dosedependent decrease in the ΔG determined, associated at the same time with an increase in the K coefficient.

The most active products of the invention reduce the glycaemia values to the level of the values of non-diabetic animals.

The results obtained are expressed in the following Table:

| PRODUCT | Demonstration of anti-diabetic activity | | | |
|---|---|---|---|---|
| | DOSE (μM/kg) | ROUTE | ΔG (g/l) | K |
| EXAMPLE 1 | 100 | i.p. | 18.24 | 2.56 |
| | 0 | | 22.82 | 1.64 |
| | 100 | i.v. | 8.54 | 2.88 |
| EXAMPLE 7 | 100 | i.p. | 12.83 | 3.25 |
| | 0 | | 20.11 | 1.53 |
| | 100 | p.o. | 17.48 | 1.56 |
| | 0 | | 23.43 | 1.1 |
| EXAMPLE 13 | 100 | i.p. | 14.39 | 2.32 |
| | 0 | | 20.88 | 1.56 |
| EXAMPLE 14 | 100 | i.p. | 17.16 | 2.96 |
| | 30 | i.p. | 20.26 | 2.26 |
| | 0 | | 23.60 | 1.19 |
| | 100 | i.v. | 6.00 | 3.27 |
| EXAMPLE 19 | 100 | i.p. | 18.60 | 2.26 |
| | 0 | | 22.02 | 1.28 |
| EXAMPLE 25 | 100 | i.p. | 12.42 | 2.09 |
| | 0 | | 20.03 | 0.9 |
| EXAMPLE 27 | 100 | i.p. | 13.76 | 1.96 |
| | 0 | | 20.61 | 1.36 |
| EXAMPLE 28 | 100 | i.p. | 9.95 | 1.81 |
| | 0 | | 19.23 | 1.21 |
| EXAMPLE 42 | 100 | i.p. | 16.58 | 2.03 |
| | 0 | | 18.25 | 1.26 |
| EXAMPLE 43 | 100 | i.p. | 17.56 | 1.97 |
| | 0 | | 19.01 | 1.19 |

EXAMPLE B

Pharmaceutical composition

Preparation formula for 1000 tablets each containing 50 mg

| compound of Example 7 | 750 g |
|---|---|
| hydroxypropylcellulose | 2 g |
| cornstarch | 10 g |
| lactose | 100 g |
| magnesium stearate | 3 g |
| talc | 3 g |

We claim:

1. A method for treating a mammal afflicted with a disease requiring a compound which improves glucose tolerance, resulting from non-insulin-dependent diabetes, comprising the step of administering to said mammal an amount of a compound selected from those of formula (I):

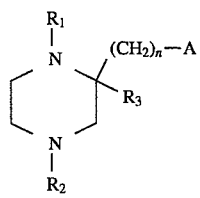

(I)

in which $R_1$ and $R_2$, each independently of the other, are selected from hydrogen, alkyl, cycloalkyl, monocyclo-alkylalkyl, dicycloalkylalkyl, aryl, and arylalkyl, each of those radicals being optionally substituted, $R_3$ is selected from hydrogen and alkyl, n has a value selected from 0, 1 and 2, and A represents

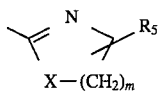

in which

X is $N-R_4$, m has a value selected from 1 and 2, $R_4$ is selected from hydrogen and optionally substituted alkyl, alkoxycarbonyl and aryloxycarbonyl, and $R_5$ is selected from hydrogen and alkyl, wherein:

the terms "alkyl", "alkoxy", "monocyclo-alkylalkyl", "dicycloalkylalkyl", "arylalkyl" and "alkoxycarbonyl" denote radicals the hydrocarbon chain of which has 1 to 10 carbon atoms inclusive in a straight or branched chain, the term "cycloalkyl" denotes a cyclic hydrocarbon radical having 3 to 8 carbon atoms inclusive, the terms "aryl", "arylalkyl", and "aryloxycarbonyl" relate to radicals the aromatic part of which is selected from phenyl and naphthyl, and the expression "optionally substituted" means that the radicals so described may be substituted by one or more chemical entities selected from alkyl, hydroxy, alkoxy, halogen haloalkyl, polyhaloalkyl, nitro, amino, alkylamino, and polyalkylamino, their stereoisomers, N-oxides, and pharmaceutically-acceptable acid or base addition salts, which is effective for alleviation of said disease.

2. A method according to claim 1 in which X represents the group $-N-R_4$ and m is 1, its stereoisomers, N-oxides, and pharmaceutically-acceptable acid or base addition salts.

3. A method according to claim 1 wherein the compound is selected from 1-(2,4-dichlorobenzyl)-2-(4,5-dihydro[1H]imidazol-2-yl)-4-methylpiperazine, its stereoisomers, N-oxides, and pharmaceutically-acceptable acid addition salts.

4. A method according to claim 1 wherein the compound is selected from 1-methyl-2-(4,5-dihydro[1H]imidazol-2-yl)-4-(2-chlorobenzyl)piperazine, its stereoisomers, N-oxides, and pharmaceutically-acceptable acid addition salts.

5. A method according to claim 1 wherein the compound is selected from 1-methyl-2-(4,5-dihydro[1H]imidazol-2-yl)-4-(2,4-dichlorobenzyl)piperazine, its stereoisomers, N-oxides and pharmaceutically-acceptable acid addition salts.

6. A method according to claim 1 wherein the compound is selected by 1,4-dibenzyl-2-[(4,5-dihydro[1H]imidazol-2-yl)-methyl]piperazine, its stereoisomers, N-oxides and pharmaceutically-acceptable acid addition salts.

7. A method according to claim 1 wherein the compound is selected from 1,4-diisopropyl-2-(4,5-dihydro[1H]imidazole-2-yl)piperazine.

* * * * *

UNITED STATES PATENT AND TRADEMARK OFFICE
CERTIFICATE OF CORRECTION

PATENT NO. : 5,500,426
DATED : Mar. 19, 1996
INVENTOR(S) : Jean-Jacques Godfroid, Aazdine Lamouri, Estera Touboul, Xuan Wang, Pierre Renard, Bruno Pfeiffer, Beatrice Guardiola It is certified that error appears in the above-indentified patent and that said Letters Patent is hereby corrected as shown below:

Column 1, line 58: "dicyclo-alylalkyl" should read
-- dicyclo-alkylalkyl --.
Page 2, line 6.
Column 5, line 55: "pan" should read -- part --.

Column 7, line 45: "and 62" should read -- and ß --.

Column 9, line 59: "fleshly" should read -- freshly --.

Column 18, line 66: "2,4-dimethyl2" should read
-- 2,4-dimethyl-2.
Column 21, line (last line of column): "in which" should read -- in which: --.
Claim 11, line 7

UNITED STATES PATENT AND TRADEMARK OFFICE
CERTIFICATE OF CORRECTION

PATENT NO. : 5,500,426
DATED : Mar. 19, 1996
INVENTOR(S) : Jean-Jacques Godfroid, Aazdine Lamouri, Estera Touboul, Xuan Wang, Pierre Renard, Bruno Pfeiffer, Beatrice Guardiola It is certified that error appears in the above-indentified patent and that said Letters Patent is hereby corrected as shown below:

Column 22, line 53: "N-oxides" should read
-- N-oxides, --.

Claim 6, line 3

Column 22, line 56: "is selected by" should read
-- is selected from --.

Claim 7, lines 1 & 3,

Column 22, line 61: Change the period to a comma and insert -- its stereoisomers, N-oxides, and pharmaceutically-acceptable acid addition salts. --
line 7.

Signed and Sealed this

Twenty-third Day of July, 1996

Attest:

BRUCE LEHMAN

Attesting Officer          Commissioner of Patents and Trademarks